United States Patent [19]

Chappel et al.

[11] Patent Number: 4,769,232

[45] Date of Patent: Sep. 6, 1988

[54] PARENTERAL FORMULATIONS OF INDOLMYCIN

[75] Inventors: Larry R. Chappel; Jay J. Rash, both of Groton, Conn.

[73] Assignee: Pfizer Inc., New York, N.Y.

[21] Appl. No.: 98,571

[22] Filed: Sep. 18, 1987

Related U.S. Application Data

[63] Continuation of Ser. No. 592,307, Mar. 22, 1984, abandoned.

[51] Int. Cl.$^4$ .............................................. A61K 31/79
[52] U.S. Cl. ....................................... 424/80; 514/376
[58] Field of Search ......................... 424/80; 514/376

[56] References Cited

U.S. PATENT DOCUMENTS

| | | | |
|---|---|---|---|
| 3,173,923 | 3/1965 | Rao et al. | 260/307 |
| 3,927,205 | 12/1975 | Ohno et al. | 424/80 |
| 3,957,972 | 5/1976 | Weber et al. | 424/80 |
| 4,049,816 | 9/1977 | Harnden et al. | 424/270 |
| 4,086,332 | 4/1978 | Armstrong | 424/80 |
| 4,126,680 | 11/1978 | Armstrong | 424/80 |

OTHER PUBLICATIONS

Merck Index 10th Ed., Monograph No. 4850.

Primary Examiner—Frederick E. Waddell
Attorney, Agent, or Firm—Peter C. Richardson; Albert E. Frost; Robert K. Blackwood

[57] ABSTRACT

Solutions of indolmycin in a pharmaceutically-acceptable solvent are of special value in the treatment of susceptible bacterial infections in mammals, particularly swine.

10 Claims, No Drawings

PARENTERAL FORMULATIONS OF INDOLMYCIN

This is a continuation of application Ser. No. 592,307, filed on Mar. 22, 1984, now abandoned.

BACKGROUND OF THE INVENTION

The present invention is concerned with solutions of indolmycin at concentrations at least 2.5% (W/V) for use in the treatment of bacterial infections in mammals, particularly swine.

Indolmycin is a known antibiotic derived by fermentation (see Merck Index, 9th Ed., Monograph No. 4843). Indolmycin was originally designated as PA 155A in U.S. Pat. No. 3,173,923, which generally discloses indolmycin formulations and their use in systemic treatment of bacterial infections, based upon low toxicity in mice and protection of mice from otherwise lethal infections.

The mouse toxicity and protection studies described in the above cited U.S. patent employed suspensions of indolmycin in so-called "Pfizer diluent", essentially the formulation of indolmycin described in Example 8 below, herein designated as formulation #8. Unfortunately, when that standard formulation was later tested for intramuscular toleration in swine, preliminary to an efficacy study, it was determined that swine injected *intramuscularly* at a dose of 20 mg/kg once daily for two days manifested severe *gastrointestinal* toxicity, as shown by severe scours, depression, anorexia, weight loss and pathology at necropsy. Even intramuscular injection of only 5 mg/kg once daily for two days resulted in gastrointestinal toxicity as reflected by the resulting scours. Control studies showed that the scours did not result from the vehicle. Indeed, subsequent studies showed that alternative suspensions, e.g., in the di(caprylate/caprate) ester of propylene glycol (formulation #4) or even in water (formulation #7), injected intramuscularly at 5 mg/kg once daily for two days, behaved similarly, or in the case of *water*, caused even more scours than the standard formulation #8.

SUMMARY OF THE INVENTION

Surprisingly, we have found that indolmycin injected intramuscularly into swine in the form of a solution in 50% aqueous 2-pyrrolidone (formulation #12, Example 12 below) at a dose of 20 mg/kg once daily for two days showed no signs of the gastrointestinal toxicity seen with the standard type of suspension noted above. Similarly, other solutions of indolmycin (formulations #1, #5, and #6, below) dosed intramuscularly at 5 mg/kg once daily for two days, showed no significant gastrointestinal toxicity, while the same dosage of suspensions of indolmycin (formulations 4, 7, and 8) invariably showed significant gastrointestinal toxicity, based on their scours scores in a comparative test. In further testing, other indolmycin solutions (formulations #2, #3, #9, #10, and #11, below) were shown to be equivalent to indolmycin solution formulation #1, again based on their scours scores in a further comparative test.

Furthermore, indolmycin dosed intramuscularly in solution at 2.5–5 mg/kg once a day for 2 days is effective in the control of a susceptible bacterial infection in swine, as illustrated by use of such a regimen in the control of an experimental *Actinobacillus pleuropneumoniae* respiratory infection in swine, as detailed below.

Based on these surprising results, the present invention is directed to formulations suitable for parenteral injection in a mammal which comprise a solution of at least 2.5% by weight/volume of indolmycin in a pharmaceutically acceptable solvent. The specified minimum concentration permits parenteral dosage of an effective amount of indolmycin, without an undue volume of solvent. For example, the dilute aqueous solution of indolmycin found in fermentation broths would not represent a suitable formulation. Preferred solvents are 2-pyrrolidone, caprolactam, glycofurol, water and N,N-dimethylacetamide, or a mixture of any two or more of said individual solvents. Most preferred as solvents are aqueous 2-pyrrolidone, aqueous caprolactam, aqueous glycofurol and aqueous N,N-dimethylacetamide. These formulations are optionally adjusted to a preferred pH range of 5.0±0.1, and optionally contain a surface active agent and/or a co-solvent. Favored as surface active agents are polyoxyethylene sorbitan fatty acid esters and polyoxyethylene glycol fatty acid esters. Representative of polyoxyethylene sorbitan fatty acid esters are the mono oleate ester (sold under the trademark Polysorbate 80), the mono stearate ester (sold under the trademark Polysorbate 60), the mono laurate ester (sold under the trademark Polysorbate 20), and the tristearate ester (sold under the trademark Polysorbate 65), all of which are available from Atlas Chemical Industries, Inc. of Wilmington, Del.

Representative of the polyoxyethyleneglycol esters are polyoxyethylene (40) stearate (sold under the trademark Polyoxyl 40 Stearate), polyoxyethylene (8) stearate, polyoxyethylene (50) stearate (all of which are available from Atlas Chemical Industries); polyoxyethylene alcohol esters such as polyoxyethylene (23) lauryl ether, polyoxyethylene (10) cetyl ether, polyoxyethylene (20) stearyl ether and polyoxyethylene (20) oleyl ether (sold under the trademarks Brij 35, Brij 56, Brij 78 and Brij 98, respectively, and available from ICI United States, Inc., Wilmington, Del. 19897). When a surface active is used, the preferred agent is Polysorbate 80.

Favored as co-solvents are 1-vinyl-2-pyrrolidone polymers (povidones), especially those having molecular weights in the range of from 10,000 to 100,000. The preferred povidones are those having molecular weights of from 12,000 to 50,000. Said surface active agents and co-solvents, when used, are employed at levels of up to 20% weight/volume.

The present invention is also directed to a method of treating or preventing bacterial pneumonia in a mammal which comprises parenteral injection of a bacterial pneumoniae curative or preventing amount of indolmycin in a solution formulation.

DETAILED DESCRIPTION OF THE INVENTION

The present solutions of indolmycin for parenteral injection in a pharmaceutical acceptable solvent are readily prepared and parenterally administered in the cure or prevention of a susceptible bacterial infection in mammals, particularly in cattle and most particularly (for the reasons stated above) in swine.

The preparation of specific solutions is illustrated below. Anyone skilled in the art will readily find additional pharmaceutically-acceptable solvents or solvent combinations which will provide at least 2.5% W/V solutions of indolmycin, with or without pH adustment to the preferred range of 5.0±0.1, and with or without the addition of up to 20% W/V of a surface active agent.

Following an initial determination that intramuscular injection of indolmycin suspended in Pfizer diluent induced severe gastrointestinal toxicity, and the discovery that a similarly dosed solution of indolmycin in a 1:1 mixture of 2-pyrrolidone:water showed little or no gastrointestinal toxicity, particularly when dosage was restricted to a two day period, a side by side comparison study of the toleration of indolmycin suspended in Pfizer diluent with indolmycin solution in 1:1 2-pyrrolidone:water was carried out.

Fourteen, healthy, nonscouring, crossbred pigs of average weight 21 kg and approximate age 10 weeks were allotted to pens of 6 or 8 pigs each, in a concrete building with forced ventilation. The swine were watered and fed ad libitum with a 16% protein swine grower ration. Of six control pigs in one pen, three received appropriate control doses of Pfizer diluent (see Example 8) and three 1:1 2-pyrrolidone:water). Of the eight medicated pigs in the other pen, four received two daily doses of 20 mg/kg of a 5% (W/V) indolmycin suspension in Pfizer diluent (formulation #8) and four a 5% (W/V) solution of indolmycin in 1:1 2-pyrrolidone:water. The pigs were observed for 7 days following the second dose for scours, for weight gain or loss, and for depression. The results are summarized in Table 1. During the test, all pigs dosed with the indolmycin suspension demonstrated profuse, prolonged scouring (many days with a scour score of 3), anorexia, weight loss, depression and rough hair coat. At the end of the test, severe gastrointestinal lesions were noted in this group on necropsy. One of the pigs dosed with indolmycin solution showed mild scouring (score of 2) on a single day, but otherwise scour scores were 0 or 1, and no gastrointestinal pathology was noted in any of the pigs on necropsy.

TABLE 1

Effects of Intramuscular Indolmycin (20 mg/kg/day for 2 days) on Scours; Depression and Weight Gain.

| Treatment[a] | Average Daily Scour Score[b] | Number of Scour Scores of "3" Per Total Observations | Depression Scores[c] | Average Weight Gain/Pig[d] |
|---|---|---|---|---|
| T1 | 0.28 | 0/18 | 0.44 | +4.5[e] |
| T2 | 0.44 | 1/18 | 0.65 | +1.7 |
| T3 | 0.38 | 0/24 | 0.30 | +6.4 |
| T4 | 2.00 | 14/24 | 1.95 | −1.6 |

[Table 1 Footnotes]
[a]Treatment Description
T1 1:1 2-pyrrolidone:water
T2 Pfizer diluent
T3 Solution in 2:1 2-pyrrolidone:water (formulation #12)
T4 Suspension in Pfizer diluent (formulation #8)
[b]Scour Scores - Fecal Consistency
0—Normal
1—Slightly loose
2—Moderately loose
3—Watery (very loose)
4—Death
[c]Depression Scores
1-3 Mild
4-6 Moderate
7-9 Severe
[d]At day 8 (end of test) unless otherwise specified.
[e]At day 4.

In a follow-up study, additional 5% idolmycin solutions and suspensions, were tested at 5 mg/kg×2 days (5 mg/kg SID×2). In this study, 36 pigs divided into groups of six pigs, average 24 kg in weight, were injected intramuscularly, in the area of the neck, with 5 mg/kg of 5% solutions or suspensions of indolmycin. Each group of six pigs was maintained in a single pen (2.5 M² of floor space/pig), watered and fed ad libitum with a 16% protein swine grower ration. The pigs were crossbred and of 10 weeks age, and had been aclimated to the facility for 20 days prior to the initiation of the experiment. Average scour sores over the 7 day observation period, and the proportion of scour scores which were greater than one are shown in a Table 2. Indolmycin suspension in Pfizer diluent was used as a positive control (Cf. table 1). Clearly, all three suspensions showed a similar, adverse scours effect, while all three solutions were virtually free of scours effect.

TABLE 2

Effects of Intramuscular Indolmycin (5 mg/kg/day for 2 days) in Scours.

| Formulation[a] | Average Daily Scour Score[b] | % of Scour Scores of "2" or greater |
|---|---|---|
| #8 (Suspension In Pfizer diluent) | 0.81 | 26.2 |
| #4 (Suspension in oil) | 0.57 | 21.4 |
| #7 (Suspension in aqueous polysorbate 80) | 1.64 | 54.8 |
| #1 (pH 5 Solution in 2:1 2-pyrrolidone:water) | 0.1 | 0 |
| #5 (pH 5 solution in 2-pyrrolidone with polysorbate 20) | 0.2 | 4.8 |
| #6 (Solution in glycofurol) | 0.2 | 4.8 |

[a]See Examples for details.
[b]See Footnote b of Table 1.

In a third study carried out in the same manner as the second study, additional solutions of indolmycin were tested in pigs with like determination of scours sores over a seven day period. In this case, an indolmycin solution in 2:1 2-pyrrolidone:water (formulation #1) was used as a positive control, demonstrating the equivalence of all of these diverse solutions, in spite of the fact that all pigs in this particular study demonstrated a low level of scours. Results are shown in Table 3.

TABLE 3

Effects of Intramuscular Indolmycin (5 mg/kg/day for 2 days) on Scours.

| Formulation[a] | Average Daily Scour Score[b] | % of Scour Scores of "2" or Greater |
|---|---|---|
| #1 (pH 5 solution in 2:1 2-pyrrolidone:water) | 0.6 | 19.0 |
| #2 (Solution in 2-pyrrolidone:water:water with povidone) | 0.4 | 14.3 |
| #3 (Solution in aqueous caprolactam) | 0.6 | 16.7 |
| #9 (Solution in aqueous dimethylformamide) | 0.4 | 9.5 |
| #10 (Solution in aqueous glycofurol) | 0.6 | 23.8 |
| #11 (Solution in aqueous 2-pyrrolidone and glycofurol) | 0.4 | 9.5 |

[a]See Examples for details.
[b]See Footnote b of Table 1.

The efficacy of a 2.5–5 mg/kg/day dose of indolmycin for 2 days in the control of and *A. pleuropneumoniae* infection in pigs was demonstrated as follows.

Sixty-six eight week old, crossbred pigs of average weight 14 kg, were challenged intranasally with *Actinobacillus pleuropneumoniae*. Freshly prepared cell suspension was instilled into the nostrils of pigs (3 ml per naris given in 1 ml increments) via a 50 ml Roux automatic syringe fitted with a plastic cannula made for the administration of cattle intranasal vaccines. The mouth and opposing nostril were held shut to force inspiration of the inoculum. The instillations were timed to coincide as closely as possible with inspirations by the pig. The challenged pigs were then injected intramuscularly with one of the following treatments: Placebo (one hour after challenge), and indolmycin solution at 1.25 or 2.5 mg/kg once daily for one or two days beginning one hour after challenge and 5 mg/kg SID×2. A 10% mortality rate (1/10) was recorded in the placebo injected group where a moderately severe pleuropneumonia was induced. A single dose of indolmycin at 1.25 mg/kg was not adequately efficacious. Treatment with 2.5 mg/kg SID×2 emerged as the minimal effective dose in this trial. Good efficacy was obtained from indolmycin therapy at 5 mg/kg SID×2 when initiated one hour after challenge. When treatment at 5 mg/kg was started 24 hours after challenge, a 4-day period of clinical improvement was noted followed by relapse and extensive pneumonia seen at necropsy. Once the relapses began, even retreatment with multiple doses of indolmycin did not control the induced pneumonia.

The present invention is illustrated by the following Examples. However, it should be understood that the invention is not limited to the specific details of these Examples.

EXAMPLE 1

Solution for Parenteral Administration (#1)

Indolmycin, 5.00 g, was dissolved in 65.00 g of 2-pyrrolidone. Glacial acetic acid, 1.00 g, and most of the water for injection were added. The observed pH was 5.0±0.1. (If needed dilute HCl or dilute KOH is added by weight to adjust the pH to 5.0±0.1). Finally, water for injection to total 36.72 g was added to yield a 5% weight/volume (5 g/100 ml) solution of indolmycin. (The amount of water is of course reduced to compensate for the amount of any dilute HCl or KOH that is used to adjust pH). This solution was assigned formulation identification #1.

EXAMPLE 2

Solution for Parenteral Administration (#2)

Indolmycin, 5.00 g, was dissolved in 55.00 g of 2-pyrrolidone and 10.00 g povidone (USP, Merck Index, 9th Ed., Monograph No. 7498). Glacial acetic acid, 1.0 g, and most of the water for injection were added. The apparent pH was adjusted to 5.0±0.1 with 0.8 g KOH in 8.00 g of water for injection. Finally, the solution was diluted with water for injection to total 28.81 g yielding 100 ml of solution containing 5 g of indolmycin, which was assigned formulation identification #2.

EXAMPLE 3

Solution for Parenteral Administration (#3)

Indolmycin, 5.00 g, was dissolved in 55.00 g of caprolactam. Glacial acetic acid, 1.00 g, was added, and the apparent pH adjusted to 5.0±0.1 with 6.4 g of KOH in 30.0 g, of water for injection. The batch was brought to final weight (104.57 g) with 7.17 g of water for injection to yield 100 ml of solution containing 5 g of indolmycin, assigned formulation identification #3.

EXAMPLE 4

Suspension for Parenteral Dosage (#4)

Finely milled indolmycin, 5.00 g, was suspended in a mixture of di(caprylate/caprate) ester of propylene glycol (87.16 g), phenol (crystalline, 0.5 g) and polyethylene glycol 300 (see Merck Index, 9th Ed., Monograph No. 7349; 0.05 g) to yield a suspension of 5 mg of indolmycin in 100 ml of suspending agent, assigned formulation identification #4.

EXAMPLE 5

Solution for Parenteral Dosage (#5)

Indolmycin, 5.00 g, was dissolved in 50.00 g 2pyrrolidone and 20.00 g polysorbate 20 (see Merck Index, 9th Ed., Monograph No. 7360). Glacial acetic acid, 1.00 g, and most of the water for injection was added. The apparent pH was 5.0±0.1, but can be adjusted to that pH range with dilute KOH or HCl, if necessary. Finally, the solution was diluted with water for injection (compensating for any added KOH or HCl) to total 329.6 g yielding 100 ml of solution containing 5 g of indolmycin, assigned formulation identification #5.

EXAMPLE 6

Solution for Parenteral Administration (#6)

Indolmycin, 5.00 g, was dissolved in 55.00 g of glycofurol (Merck Index, 9th Ed., Monograph No. 4332) and made up to 100 ml with 46.80 g of water for injection. The solution was assigned formulation identification #6.

EXAMPLE 7

Suspension for Parenteral Administration (#7)

Indolmycin, 5.00 g, finely milled, was suspended in a mixture of 78.35 g of water for injection and 20.00 g of polysorbate 80 (Merck Index, 9th Ed., Monograph No. 7360) to yield 100 ml of suspension, assigned formulation identification #7.

EXAMPLE 8

Suspension for Parenteral Administration (#8)

Indolmycin, 5.00 g, finely milled, was suspended in a mixture of sodium carboxymethylcellulose type 7 LF (USP; 0.963 g), methylcellulose 15 (USP; 0.048 g), NaCl (0.867 g), polysorbate 80 (0.096 g) and water for injection, 94.937 g, to yield 100 ml of suspension containing 5 g indolmycin, assigned formulation identification #8. The suspension media is herein called "Pfizer diluent."

EXAMPLE 9

Solution for Parenteral Administration (#9)

Indolmycin, 5.00 g, was dissolved in 65.00 g N,N-dimethylacetamide. Glacial acetic acid, 1.00 g, and most of the water for injection were added. The apparent pH was adjusted to 5.0±0.1 with 2 mg of HCl in 0.20 g of water. The solution was made up to 100 ml with 28.74 g water for injection and assigned formulation identification #9.

EXAMPLE 10

Solution for Parenteral Administration (#10)

Indolmycin, 5.00 g, was dissolved in 70.00 g glycofurol. Glacial acetic acid, 1.00 g, and most of the water for injection were added. The apparent pH was adjusted to 5.0±0.1 with 2 mg HCl in 0.20 g of water. The solution was made up to 100 ml with a total of 32.28 g of water for injection and assigned formulation identification #10.

EXAMPLE 11

Solution for Parenteral Administration (#11)

Indolmycin, 5.00 g, was dissolved in a mixture of 35.00 g of 2-pyrrolidone and 30.00 g of glycofurol. Glacial acetic acid, 1.00 g, and most of the water for injection were added. The apparent pH was adjusted to 5.0±0.1 with 0.8 g KOH in 8.00 g water for injection. The solution was made up to 100 ml with a total of 30.63 g of water for injection, and assigned formulation identification #11.

EXAMPLE 12

Solution for Parenteral Administration (#12)

Indolmycin, 2.5 g, was made up to 50 ml with 50% pyrrolidone/water (V/V), warmed slightly, and dissolved on a vortex mixer to yield 50 ml of solution containing 2.5 g of indolmycin (5% W/V), assigned formulation identification #12.

In like manner, indolmycin, 1 g, was dissolved in 10 ml of 70% pyrrolidone/water (V/V) to yield a 10% (W/V) solution of indolmycin. The pH was 8.05.

In like manner, indolmycin, 2.5 g, is dissolved in 50% pyrrolidone/water (V/V) to yield a 2.5% (W/V) solution of indolmycin.

We claim:

1. A method of treating or preventing bacterial pneumonia in swine which comprises intramuscular injection of a bacterial pneumonia curative or preventing amount of indolmycin in a formulation which comprises a solution of at least 2.5% by weight/volume of indolmycin in a pharmaceutically-acceptable solvent.

2. A method of claim 1 wherein the solvent is 2-pyrrolidone, caprolactam, glycofurol, water, N,N-dimethylacetamide, or a mixture of two or more thereof.

3. A method of claim 2 wherein the solvent is 2-pyrrolidone and water.

4. A method of claim 2 wherein the solvent is caprolactam and water.

5. A method of claim 2 wherein the solvent is glycofurol and water.

6. A method of claim 2 wherein the solvent is N,N-dimethylacetamide and water.

7. A method of claim 1 wherein the formulation further comprises a surface active agent.

8. A method of claim 2 wherein the formulation further comprises a surface active agent.

9. A method of claim 8 wherein the surface active agent is up to 20% weight/volume of povidone or a polysorbate polymer.

10. A method of claim 9 wherein the solvent is 2-pyrrolidone and water.

* * * * *